United States Patent
Haid, Jr. et al.

(10) Patent No.: US 6,197,033 B1
(45) Date of Patent: Mar. 6, 2001

(54) GUIDE SLEEVE FOR OFFSET VERTEBRAE

(75) Inventors: Regis W. Haid, Jr., Atlanta, GA (US); Christopher Comey, Springfield, MA (US); Bradley T. Estes, Memphis, TN (US); Jeffrey D. Moore, Horn Lake, MS (US); Eddie F. Ray, III, Cordova, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/287,927

(22) Filed: Apr. 7, 1999

Related U.S. Application Data

(60) Provisional application No. 60/081,206, filed on Apr. 9, 1998.

(51) Int. Cl.$^7$ .................................................. A61B 17/58
(52) U.S. Cl. ................................................. 606/99; 606/61
(58) Field of Search ................... 606/61, 99, 79, 606/96, 80; 623/17.11, 12, 13, 14, 15, 16, 17, 18, 19

(56) References Cited

U.S. PATENT DOCUMENTS

| | | | |
|---|---|---|---|
| 5,601,556 | 2/1997 | Pisharodi | 606/61 |
| 5,669,915 | * 9/1997 | Caspar et al. | 606/96 |

FOREIGN PATENT DOCUMENTS

WO 9627321   9/1996   (WO) .

* cited by examiner

*Primary Examiner*—Gary Jackson
*Assistant Examiner*—Anthony S. King
(74) *Attorney, Agent, or Firm*—Woodard, Emhardt, Naughton, Moriarty & McNett

(57) ABSTRACT

A guide sleeve with longitudinally offset bone engaging portions is provided for engagement with anterior-posterior offset vertebral bodies. In one aspect of the invention the guide tube has fixed bone engaging portions in a predetermined offset position. In another form of the invention, the guide sleeve is composed of at least two moveably connected portions adapted to permit adjustment of the offset between the bone engaging portions. Further, a method is provided for using a guide sleeve with offset bone engaging portions.

16 Claims, 4 Drawing Sheets

GUIDE SLEEVE FOR OFFSET VERTEBRAE

CROSS-REFERENCE TO RELATED APPLICATION

This application claims the benefit of U.S. Provisional Application No. 60/081,206, filed Apr. 9, 1999.

BACKGROUND OF THE INVENTION

The present invention relates generally to surgical procedures for spinal stabilization and more specifically to instrumentation adapted for inserting a spinal implant within the intervertebral disc space between adjacent vertebrae. More particularly, while there may be other applications, the present invention is especially suited for engaging two vertebral bodies that are offset in an anterior-posterior fashion, as in spondylolisthesis, with respect to each other and providing a protected passageway for the movement of instruments and implants therethrough.

Currently available systems utilize a hollow sleeve having a uniform bone engaging end with teeth extending therefrom to be driven into the vertebrae adjacent the disc space. However, a common condition in spinal abnormalities is that adjacent vertebral bodies have been displaced creating an anterior-posterior offset condition. While offset vertebral bodies may be encountered in any part of the spine as a result of trauma, disease, or degeneration, the condition of spondylolisthesis typically develops in the lumbar spine. With offset vertebral bodies, the uniform bone engaging end of the hollow sleeve in prior systems, adapted to engage anterior-posterior aligned vertebral bodies, fails to completely engage both offset vertebra bodies simultaneously. This incomplete engagement with the offset vertebral bodies creates an unprotected space between one of the vertebral bodies and the end of the hollow sleeve. This unprotected space may allow contact between instruments disposed within the sleeve, such as cutting instruments, and surrounding tissue. Such contact may damage the sensitive tissue adjacent to the vertebral body leading to potential injury or death for the patient.

While the more recent techniques and instrumentation represent an advance over earlier surgical procedures for protecting surrounding tissue during preparation of the disc space and insertion of a fusion device, the need for improvement still remains. The present invention is directed to this need and provides a more effective protective guide sleeve for engaging offset vertebral bodies.

SUMMARY OF THE INVENTION

The present invention provides a guide sleeve having offset bone engaging portions. In one aspect the sleeve comprises a first tube portion having a first bone engaging end and a second tube portion moveably connected to the first tube portion. The second tube portion includes a second bone engaging end disposed proximal to the first bone engaging end. The second tube portion is moveable in relation to the first bone engaging portion to create an offset between the second bone engaging surface in relation to the first bone engaging surface. Preferably, the bone engaging end will include a distraction portion extending distally therefrom. Optionally, the guide sleeve may define one or more windows for visualization.

In another aspect, the invention provides a sleeve composed of a tube having a longitudinal axis and a bone engaging end. The bone engaging end has a first bone engaging portion and a second bone engaging portion. The second bone engaging portion is offset with respect to the first bone engaging portion. Preferably, the offset bone engaging portions are adapted to engage offset vertebral bodies.

Still further, the present invention provides a method of positioning a guide sleeve against a first vertebral body offset from a second vertebral body. The method includes making a determination of the amount of offset between the first vertebral body and the second vertebral body. A guide sleeve is provided that includes a bone engaging portion with a first portion and a second portion longitudinally offset from the first portion, the offset between the first and second portions substantially corresponding to the offset between the first vertebral body and the second vertebral body. The guide sleeve is then positioned adjacent the spine with the first bone engaging portion engaging the first vertebral body and the second bone engaging portion engaging the second vertebral body. Optionally, the guide sleeve may be composed of a first portion slidably connected to a second portion. In this configuration, the amount of offset may be adjusted to correspond to the offset between adjacent vertebra. Additionally, it is contemplated that with a moveable first portion, the extent of offset between the bone engaging portion may be adjusted after insertion into the body.

One object of the present invention is to provide an improved guide sleeve for engaging offset bone segments.

Related objects and advantages of the present invention will be apparent from the following description.

DESCRIPTION OF THE PREFERRED EMBODIMENTS

Figure 1:
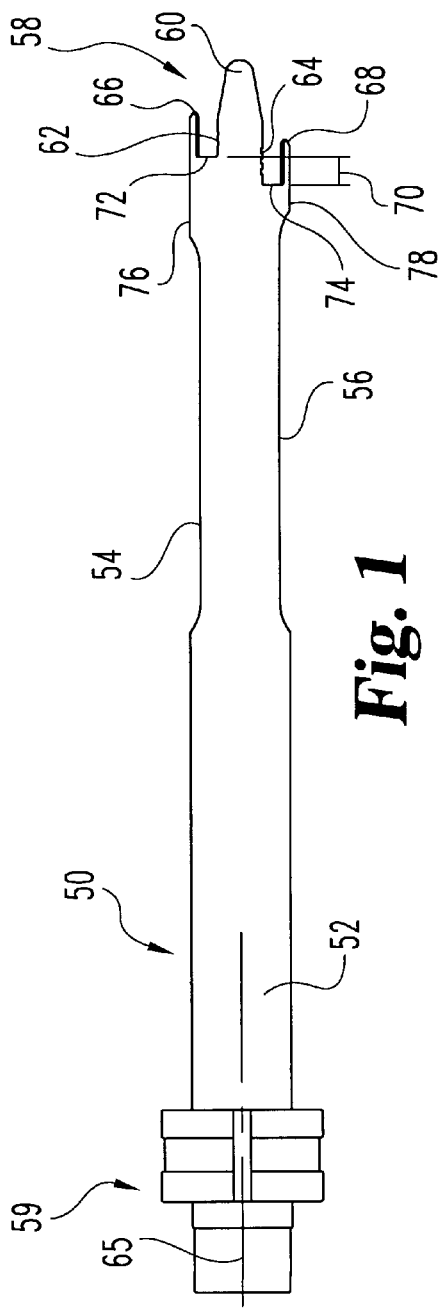
FIG. 1 is a side elevational view of an offset guide sleeve according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

The present invention provides a guide sleeve for guiding instruments to a surgical site and protecting surrounding tissue from injury as a result of contact with the instruments disposed within the sleeve. While the invention may have other applications, particularly in the spine, in one preferred embodiment the invention is specifically adapted to engage anterior-posterior offset vertebral bodies to define a protected access passage to the disc space between the offset vertebral bodies. Provisional application 60/081,206 filed Apr. 9, 1998 and related utility application 09/179,799 entitled METHOD AND INSTRUMENTATION FOR POSTERIOR INTERBODY FUSION, filed Oct. 27, 1998, are incorporated herein by reference.

Figure 2:
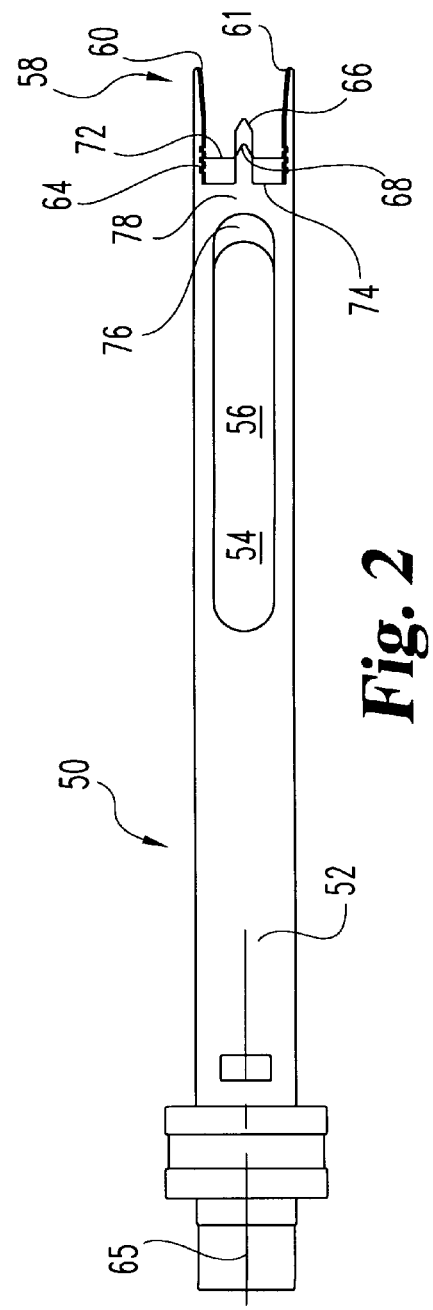
FIG. 2 is a side elevational view of the sleeve of FIG. 1 rotated 90° about the longitudinal axis.

FIGS. 1 and 2 illustrate a guide sleeve in accordance with a preferred embodiment of the invention. Specifically, guide sleeve 50 includes a tube body 52 defining a bone engaging end 58 and an opposite proximal end 59. Tube body 52 defines a longitudinal axis 65 extending between bone engaging end 58 and proximal end 59, as well as a longitudinally extending internal working channel 53 (FIG. 2a) adapted to receive surgical instruments. Preferably, tube body 52 defines windows 54 and 56 extending through the tube side walls. Windows 54 and 56 provide access through the tube for external visualization of instruments disposed within the tube, visualization of the disc space and instrument access for debridement. Smaller window 54 is offset along longitudinal axis 65 from bone engaging end 58 by side wall portion 76. Similarly, larger window 56 is offset along longitudinal axis 65 from bone engaging end 58 by side wall portion 78. Side wall portion 76 is longer than side wall portion 78 and thus provides greater protection against the intrusion of neural tissue into the working channel of guide sleeve 50.

Figure 2A:
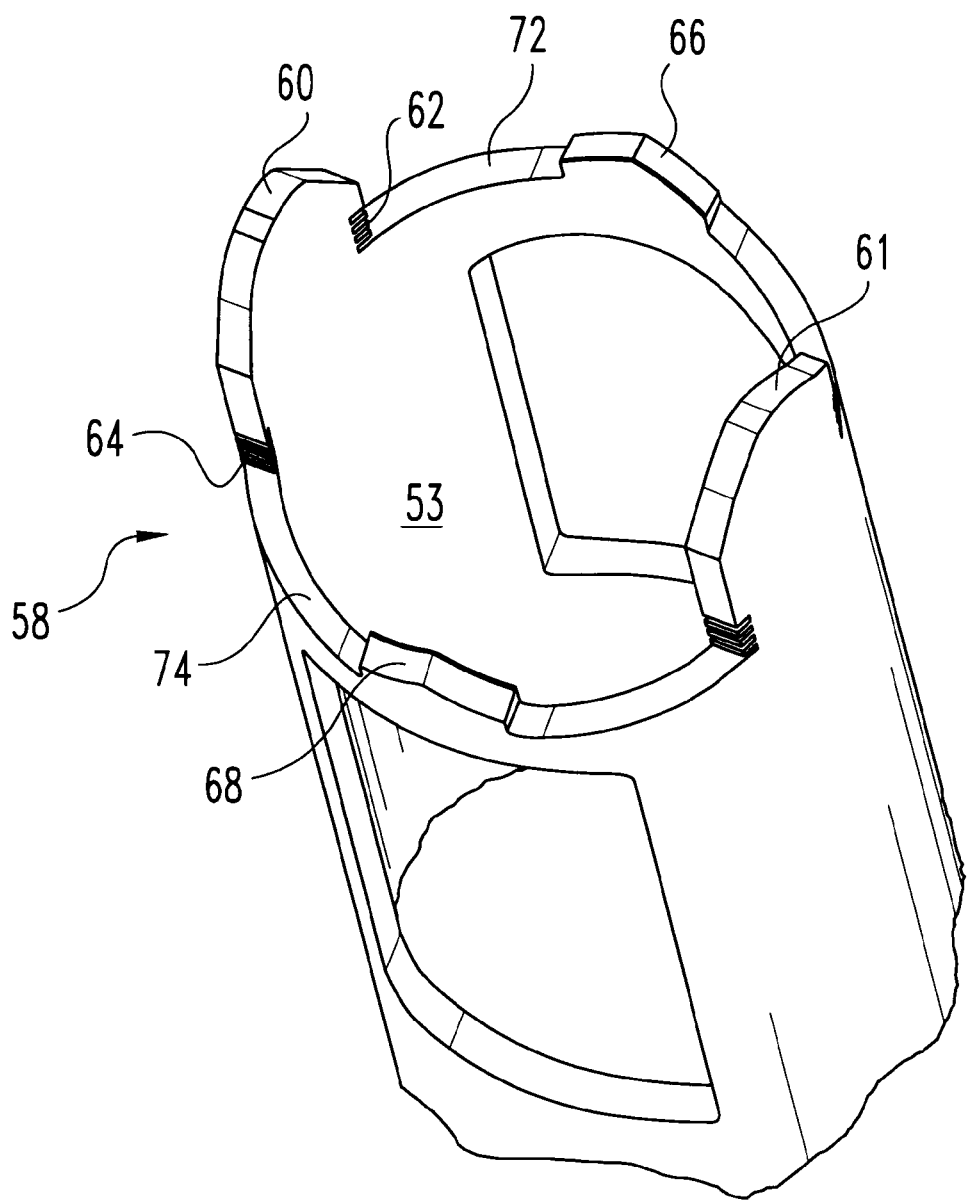
FIG. 2a is an enlarged perspective view of the bone engaging end of FIG. 2.

Referring now more specifically to FIG. 2a showing an enlarged view of bone engaging end 58, in a preferred embodiment the bone engaging end includes a pair of opposing distraction extensions 60 and 61 having tapered leading tips to ease insertion into the disc space. Optionally, distraction extension 60 includes offset groove portions 62 and 64 to engage the adjacent vertebral bodies and resist expulsion from the disc space. Distraction extension 61 is similarly configured. Distraction extension 60 terminates on a first side adjacent bone engaging surface 72 and on a second side adjacent bone engaging surface 74. Distraction extension 61 is similarly configured and terminates adjacent bone engaging surfaces 72 and 74. Preferably, bone engaging surfaces 72 and 74 each have a substantially planar configuration interrupted by spikes 66 and 68, respectively. While other geometries of guide tube 50 are contemplated, such as but without limitation square and rectangular, the end configuration in the preferred embodiment is substantially circular in cross section and defines a cylindrical internal working channel. Preferably, distraction extensions 60 and 61 are configured to have the same extent of longitudinal extension (FIG. 2).

As shown most clearly in FIG. 1, bone engaging surfaces 72 and 74 are longitudinally offset by a distance 70. Preferably, each bone engaging surface 72 and 74 includes a spike 66 and 68, respectively, for penetrating the vertebral bone. The tips of spikes 66 and 68 are likewise offset by a distance approximate to distance 70. While spikes have been shown in a preferred embodiment, it is contemplated that spikes are not required to utilize the present invention. Moreover, although one spike has been shown on each surface, those skilled in the art will understand that more or less spikes or other bone engaging structures may be utilized on the bone engaging surfaces without deviating from the spirit and scope of the invention.

Bone engagement ends 72 and 74 are offset a distance 70 that is selected to approximate the amount of anterior-posterior displacement between adjacent vertebral bodies. It will be understood that a series of guide sleeves 50 may be provided, each having a different displacement 70, such that the appropriate guide sleeve 50 may be selected depending upon the amount of anterior-posterior offset between adjacent vertebra determined during examination of the vertebral bodies.

Figure 3:
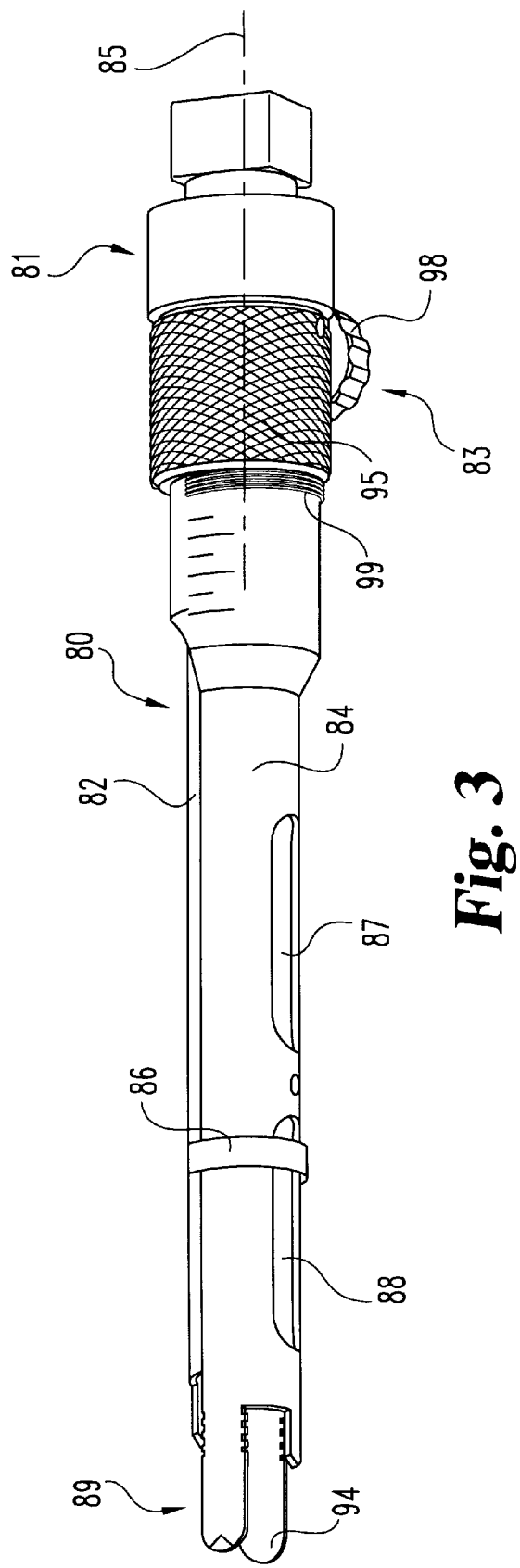
FIG. 3 is a side view of an alternative embodiment of an offset guide sleeve engaged in a vertebral column.
Figure 4:
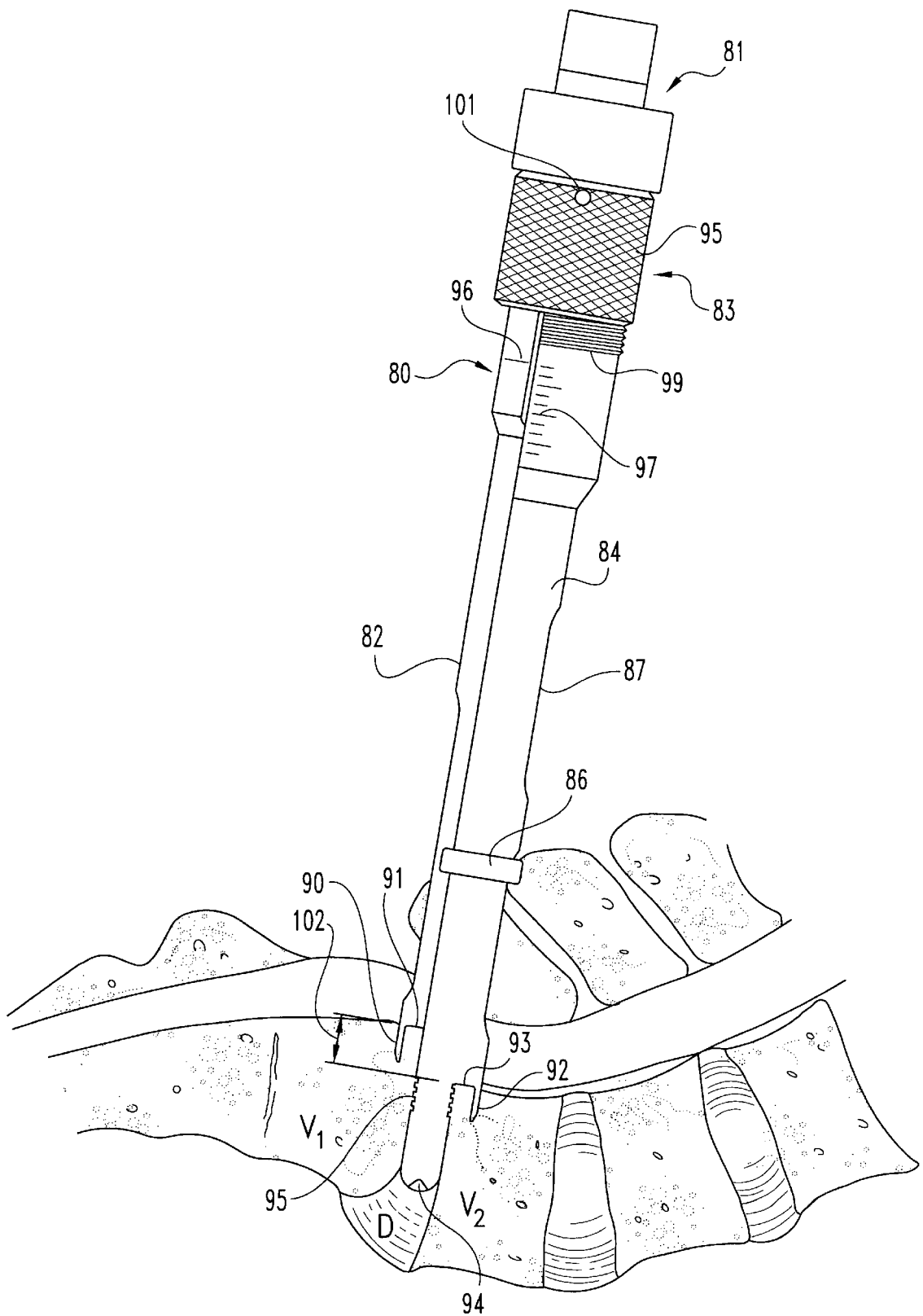
FIG. 4 is a perspective view of the guide sleeve of FIG. 3 engaged in a vertebral column.

Referring now to FIGS. 3 and 4, there is shown yet a further preferred embodiment of a guide sleeve according to the present invention. Guide sleeve 80 includes first end 81 and an opposite bone engaging end 89 and a longitudinal axis 85 extending therebetween. Guide sleeve 80 is divided into a fixed portion 82 and a movable portion 84. In a preferred embodiment, fixed portion 82 and movable portion 84 are configured to define the side walls of a cylindrical tube to thereby form 360 degrees of protection. However, it is contemplated that one of the portions may form the complete guide tube with a segment thereof being movable to adjust the configuration of bone engaging end 89. The proximal portion of fixed moveable portion 84 is maintained in alignment with fixed portion 82 by adjustment mechanism 83. The distal portion of moveable portion 84 is maintained in alignment with fixed portion 82 by distal guide 86.

Guide sleeve 80 also includes visualization windows 87 and 88 formed in movable portion 84 and an opposing visualization window formed in fixed portion 82. The bone engaging end 89 is configured similar to the bone engaging end 58 of guide sleeve 50 previously described. Bone engaging end 89 includes a pair of distraction extensions 94. In the illustrated embodiment, distraction extensions 94 do not include the tapered sections adjacent the distal tip as shown with respect to guide sleeve 50. However, it is contemplated that such a configuration may be used if it is desirable to ease insertion of the distraction extensions into the disc space. Fixed portion 82 includes bone engaging surface 91 having a spike 90. Moveable portion 84 includes bone engaging surface 93 having a spike 92.

The position of moveable portion 84 relative to fixed portion 82 is adjusted by adjustment mechanism 83 disposed adjacent proximal end 81. Adjustment mechanism 83 includes an internally threaded collar 95 rotatably mounted on sleeve 80 by several pins similar to pin 101 engaging an internal shoulder (not shown). Collar 95 is adapted to engage external threads 99 disposed on movable sleeve 84. It will be understood that as internally threaded collar 95 is rotated about guide sleeve 80, moveable portion 84 will move axially with respect to fixed portion 82 in relation to the thread pitch. In this manner the offset 102 between bone engaging surfaces 91 and 93 can be adjusted. The combination of mark 96 on fixed portion 82 and scale 97 on movable portion 82 provides an indication of the amount of displacement between fixed portion 82 and movable portion 84, and the corresponding offset 102 between bone engaging surfaces 91 and 93. Collar 95 may be prevented from rotation by use of lock 98 which consists of a threaded shaft (not shown) with an external knob. The threaded shaft is received in a threaded opening in collar 95 and may be advanced to prevent rotation of the collar and thereby securely lock the offset in the desired position.

Referring now to FIG. 4, an imaging system may be utilized to determine the anterior-posterior offset 102 between adjacent lower vertebral body $V_1$ and upper vertebral body $V_2$. Once offset 102 has been determined, a fixed guide sleeve 50 having a longitudinal offset 70 between a lower bone engaging end 74 and an upper bone engaging end 72 approximating offset 102 may be selected or an adjustable guide sleeve 80 may be adjusted to provide a longitudinal offset 102. While a guide sleeve according the embodiment shown in FIGS. 1 and 2 may be used in a similar manner, for the purposes of illustration the following description will be made with specific reference to the embodiment illustrated in FIGS. 3 and 4.

Surgical access to the spine is achieved by known methods. In FIG. 4, the surgical procedure is performed from the posterior side of the spine. Typically, as known in the art, a distractor with the desired distraction height will be inserted into the disc space D to accomplish distraction. Guide sleeve 80 having offset 102 and distraction extensions substantially matching the distractor height is then passed over the distractor and positioned adjacent the spine. Force is then applied to proximal end 81, such as by mallet or other instrument if manual force is insufficient, to urge distraction extensions 94 into the disc space and spikes 90 and 92 into vertebral bodies $V_1$ and $V_2$, respectively. Preferably, spikes 90 and 92 will be advanced into the vertebral bodies until at least a portion of bone engaging surfaces 91 and 93 are abuttingly engaged with vertebral bodies $V_1$ and $V_2$, respectively.

In an alternative method, particularly where imaging of the disc space is inadequate, guide sleeve 80 may be adjusted once it is in position in the disc space. In this use, it is contemplated that movable portion 84 would be substantially advanced distally. Guide sleeve 80 would be advanced with distraction extensions 94 entering the disc space until contact between spike 92 and vertebra $V_2$ is achieved. Spike 90 would then be in contact with vertebra $V_1$. The adjustment mechanism may then be locked and force applied to the proximal end 81 of guide sleeve 80 to fully seat the guide sleeve in position.

Guide sleeves according to the present invention are preferably made of biocompatible materials having sufficient strength to withstand the forces encountered during insertion and use. More preferably, the guide sleeves may be made of stainless steel, titanium, or aluminum. Further, while distraction extensions and spikes have been illustrated in the preferred embodiments, it will be understood that such features are not required and that guide sleeves according to the present invention may be formed without these features. Still further, the teaching of the present invention may be applied to double barrel guide sleeves, typically utilized in anterior procedures, to provide similar advantages for adjusting the bone engaging end of the guide sleeves to accommodate various configurations of the vertebral bodies.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A sleeve for engagement with two adjacent vertebrae, said sleeve comprising:
   a first tube portion having a first bone engaging end; and
   a second tube portion movably coupled to said first tube portion, said second tube portion having a second bone engaging end disposed proximal said first bone engaging end, wherein said second tube portion is movable in relation to said first tube portion to provide a longitudinal offset between the first bone engaging portion and the second bone engaging portion.

2. The sleeve of claim 1, wherein said first bone engaging end includes a pair of opposing distraction extensions adapted for insertion into the disc space.

3. The sleeve of claim 2, wherein said first tube portion is an upper portion adapted to engage an upper vertebral body and said second tube portion is a lower portion adapted to engage a lower vertebral body.

4. The sleeve of claim 1, further including an adjustment mechanism disposed between said first tube portion and said second tube portion, said adjustment mechanism adapted to control the longitudinal extent of offset between said first bone engaging end and said second bone engaging end.

5. The sleeve of claim 4, wherein said second tube portion includes an external thread and said adjustment mechanism includes an internally threaded collar mounted on said first tube portion for controlling the position of said second tube portion with respect to said first tube portion.

6. The sleeve of claim 1, wherein said first tube portion has an upper surface defining a first window spaced from said first bone engaging end by a first side wall portion having a first longitudinal length, and said second tube portion has a lower surface defining a second window spaced from said second bone engaging end by second side wall portion having a second longitudinal length, said second length greater than said first length.

7. The sleeve of claim 1, wherein said first bone engaging end includes a first spike for piercing the bone and said second bone engaging portion includes a second spike for piercing the bone.

8. The sleeve of claim 1, wherein said first tube portion includes a plurality of index markings and said second tube includes an indicator disposed adjacent said index markings, said indicator cooperable with said index markings to indicate the longitudinal offset between said first bone engaging portion and said second bone engaging portion.

9. A guide sleeve for engaging an upper vertebra and a lower vertebra with an anterior-posterior offset therebetween, the guide sleeve comprising:
   a tube having a longitudinal axis and a bone engaging end, said bone engaging end having a first bone engaging portion for engaging the upper vertebra and a second bone engaging portion for engaging the lower vertebra, said second bone engaging portion longitudinally offset with respect to said first bone engaging portion.

10. The sleeve of claim 9, wherein said bone engaging end includes a spike for engaging a vertebral body.

11. The sleeve of claim 9, wherein said bone engaging end further includes extensions for extending into the disc space between two adjacent vertebra.

12. The guide sleeve of claim 9, wherein said first bone engaging portion is slidable longitudinally with respect to said second bone engaging portion.

13. A guide sleeve, comprising:
   a hollow tube having a longitudinal axis, said tube having a bone engaging end, said bone engaging end having a first portion and an interconnected second portion, said second portion movable with respect to said first portion to a longitudinally offset position, adapted for engagement with offset vertebra.

14. A method of positioning a guide sleeve against a first vertebral body offset from a second vertebral body, said method comprising:
   determining the amount of offset between the first vertebral body and the second vertebral body;
   providing a guide sleeve with a sleeve longitudinal axis, the sleeve having a bone engaging portion with a first portion and a second portion longitudinally offset substantially corresponding to the offset between the first vertebral body and the second vertebral body; and
   positioning the guide tube adjacent the spine with the first bone engaging portion engaging the first vertebral body and the second bone engaging portion engaging the second vertebral body.

15. The method of claim 14, wherein the guide sleeve includes distracting extension and said positioning includes inserting the distracting extensions into the disc space between adjacent vertebrae.

16. The method of claim 14, wherein said first bone engaging portion is slidable with respect to said second bone engaging portion to vary the extent of longitudinal offset therebetween and said providing includes sliding the first bone engaging portion with respect to the second bone engaging portion to approximate the offset between the first vertebral body and the second vertebral body.

* * * * *